United States Patent [19]
Fortunko et al.

[11] 4,218,924
[45] Aug. 26, 1980

[54] ULTRASONIC ELLIPSOMETER

[75] Inventors: Christopher M. Fortunko, Albuquerque, N. Mex.; Carmine F. Vasile; Robert B. Thompson, both of Thousand Oaks, Calif.

[73] Assignee: Rockwell International Corporation, El Segundo, Calif.

[21] Appl. No.: 54,394

[22] Filed: Jul. 2, 1979

[51] Int. Cl.$^3$ ............................................. G01N 29/04
[52] U.S. Cl. ...................................... 73/642; 73/643
[58] Field of Search ................................ 73/643, 642

[56] References Cited

U.S. PATENT DOCUMENTS

| | | | |
|---|---|---|---|
| 3,697,867 | 10/1972 | Kleesattel | 73/643 |
| 4,127,035 | 11/1978 | Vasile | 73/643 |
| 4,149,421 | 4/1979 | Böttcher et al. | 73/643 |

OTHER PUBLICATIONS

"Circularly Polarized Ultrasonic Shear Waves in Metal", by Thomas et al. from Physical Review Letters, vol. 20, pp. 207-208, Jan. 1968.

Primary Examiner—James J. Gill
Attorney, Agent, or Firm—L. Lee Humphries; Craig O. Malin; John J. Deinken

[57] ABSTRACT

Disclosed is an electromagnetic acoustic transducer for generating and detecting an elliptically polarized ultrasonic wave in an electrically conductive material. The transducer includes a row of uniformly sized, adjacent, alternately oriented permanent magnets, which establish a periodic magnetic field. Coaxially wound around the row is a first coil for inducing an alternating current perpendicular to the field and perpendicular to the periodic direction, while a second coil is wound around the coil orthogonal to the first coil to induce an alternating current perpendicular to the field and parallel to the periodic direction. An ultrasonic ellipsometer includes such a dual coil transmitting transducer for generating an elliptically polarized wave and a dual coil receiving transducer for detecting the wave after it has propagated through an electrically conductive medium. By using the ellipsometer to generate an elliptically polarized wave in a material and detect the change in polarization of the wave after propagating through the material, the apparatus can be employed to examine surface properties of the material.

14 Claims, 6 Drawing Figures

ULTRASONIC ELLIPSOMETER

GOVERNMENT INTEREST

The Government has rights in this invention pursuant to Contract No. DAA25-76-C0381 awarded by the United States Army.

BACKGROUND OF THE INVENTION

This invention relates to ultrasonics and, more particularly, to the generation and detection of ultrasonic waves in materials.

Precision measurements useful for evaluating elastic properties of the surface of a material are difficult to obtain. Small changes in the physical properties of a medium, however, have been precisely measured by sensing a relative shift in the phase or amplitude of two orthogonally polarized waves which occurs when such waves interact with the medium. In an optical ellipsometer, for example, a series of polarizers and quarter wave plates are utilized to measure a change in the elliptical polarization of an optical beam, which is caused as a result of the reflection of the beam from a metallic surface. Such a change occurs because the orthogonal components of the light beam, which are polarized parallel and perpendicular to the plane of incidence, exhibit identical propagation properties in a medium such as air, but are affected differently upon reflection by such a surface. Using this technique to measure such changes, foreign layers as thin as one atomic thickness, $10^{-3}$ $\mu$m or less, can readily be detected on a reflecting metal surface.

In an isotropic solid, ultrasonic shear elastic waves conceivably could be employed in an analogous manner to sense surface properties of the material, since ultrasonic waves will propagate in a solid with two different polarizations having equal propagation velocities. Three major difficulties, however, have in the past prevented the application of this technique to ultrasonic waves travelling in solid media. First, longitudinal as well as transverse ultrasonic waves will propagate in a solid. Second, in contrast to the optical isotropy of air, most polycrystalline solids contain small anisotropies which can cause the two ultrasonic waves to travel with different velocities. Measurements of shear wave birefringence, for example, are well known and have even been used to detect body stresses in solid materials. Consequently, the effects of bulk as well as surface properties of the test material are represented in known elastic wave techniques. Finally, elastic wave generating and detecting devices analogous to optical polarizer—quarter wave plate combinations have not heretofore been available in the art. Thus, piezoelectric transducers, for example, which are typically used for generating such waves, can be used to excite or detect ultrasonic waves having a fixed polarization, but the plane of the piezoelectrically generated wave polarization cannot be altered without physically rotating the piezoelectric transducer and reestablishing the mechanical bond necessary with such a system.

Therefore, a need has developed in the art for an ultrasonic transducer capable of generating an elliptically polarized wave whose polarization may be readily and conveniently adjusted.

Furthermore, it would be advantageous to provide a transducer which avoids the difficulties associated with the generation of longitudinal waves and with the birefringence effects caused by anisotropies in solids.

SUMMARY OF THE INVENTION

It is a general object of this invention to provide a new and improved ultrasonic ellipsometer and a transducer for use therein.

An electromagnetic acoustic transducer for generating and detecting an elliptically polarized ultrasonic wave in an electrically conductive material, according to the present invention, includes a source of magnetic flux for establishing a magnetic field directed normal to a surface of the material and periodic in intensity in a direction perpendicular to the field direction, a first conductor for inducing a first alternating current in a first current direction within the material perpendicular to the field direction and perpendicular to the periodic direction, and a second conductor for inducing a second alternating current in a second current direction within the material parallel to the periodic direction.

In a more particular embodiment, the magnetic field is provided by a row of alternately oriented, uniformly sized, adjacent permanent magnets. The first conductor is a first coil coaxially wound around the row and the second conductor is a second coil wound around the row orthogonal to the first coil.

An ultrasonic ellipsometer, according to the invention, includes a dual coil transmitting electromagnetic acoustic transducer for generating an elliptically polarized wave in an electrically conductive medium, and a dual coil receiving electromagnetic acoustic transducer for detecting the wave in the medium at a distance from the transmitting transducer.

The ellipsometer may further include a high frequency signal generator for driving the transmitting transducer, a signal splitter for coupling the generator to the first and second transmitting coils with a variable relative amplitude and phase, and a signal analyzer connected to the first and second receiving coils for indicating the polarity of the detected wave.

A method for generating an elliptically polarized ultrasonic shear wave in an electrically conductive medium, according to the present invention, includes the steps of:

(a) establishing a magnetic field directed normal to a surface of the medium and periodic in intensity in a direction parallel to the surface;

(b) inducing a first alternating current in a first current direction within said material perpendicular to the field direction and perpendicular to the periodic direction; and (c) inducing a second alternating current in a second current direction within said material perpendicular to the field direction and parallel to the periodic direction.

The method may further include the step of controlling the amplitude and phase of the first alternating current relative to the second alternating current to adjust the polarization of the generated wave.

Examples of the more important features of the invention have been broadly outlined in this summary in order to facilitate an understanding of the detailed description that follows and so that the contributions which this invention provides to the art may be better appreciated. There are, of course, additional features of the invention, which will be described below and which are included within the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DESCRIPTION OF THE PREFERRED EMBODIMENTS

Figure 1:
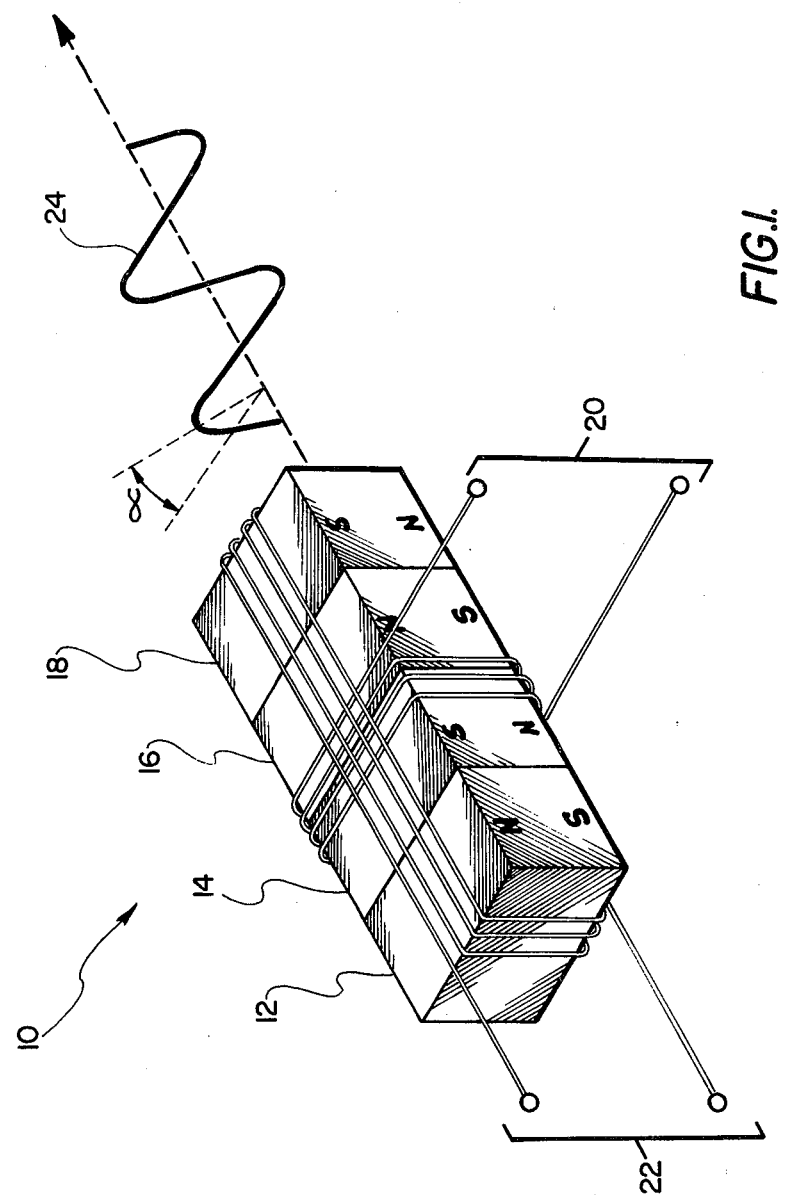
FIG. 1 is a perspective view of a dual coil electromagnetic acoustic transducer constructed according to the present invention.

Referring now to FIG. 1, illustrated in a perspective view is an electromagnetic acoustic transducer 10 (commonly referred to as an EMAT), which is designed according to the present invention to generate or detect an elliptically polarized ultrasonic wave in an electrically conductive material. The transducer 10 is of the periodic permanent magnet type, as disclosed in U.S. Pat. No. 4,127,035, the teaching of which is incorporated herein by reference. The transducer includes a row of uniformly sized, adjacent, alternately oriented permanent magnets 12, 14, 16 and 18. The magnets create a magnetic field which is directed normal to the surface of a material on which the transducer is placed and which is periodic in intensity, due to the alternate orientation of the magnets, in a direction perpendicular to the direction of the magnetic field.

Coaxially wound around the row of magnets is a first coil 20, which will convey an applied current in a circular path within the magnetic field, the applied current in turn inducing a first alternating current in a first current direction within an underlying material perpendicular to the field direction and the periodic direction. A second coil 22 is wound around the row in a direction orthogonal to the first coil 20, so that a current applied to the coil 22 will follow a circular path through the magnetic field which is orthogonal to the first current path. The current in the coil 22 will in turn induce a second alternating current in a second current direction within the material which is perpendicular to the field direction and parallel to the periodic direction.

When the first coil 20 is driven by a dynamic current of frequency f, vertically polarized shear (SV) waves are generated in an adjacent conducting medium at an angle $$\theta = \text{Sin}^{-1}(V_s/fD) \quad (1)$$

with respect to the surface normal. $V_s$ in equation (1) is the shear wave velocity in the material, while D is the period of the transducer 10 (twice the width of one permanent magnet in the row). When the second coil 22 is also driven by a dynamic current at the same frequency, a horizontally polarized shear (SH) wave is generated at the same angle. Because of the principle of wave superposition, the SV wave and the SH wave will combine to create a composite wave 24. The wave 24 may be established at any desired elliptical polarization α by simultaneously driving the two coils with signals having an appropriate relative phase and amplitude. By a reciprocal process, the same transducer design may be utilized to detect a shear wave having any arbitrary elliptical polarization.

Figure 2:
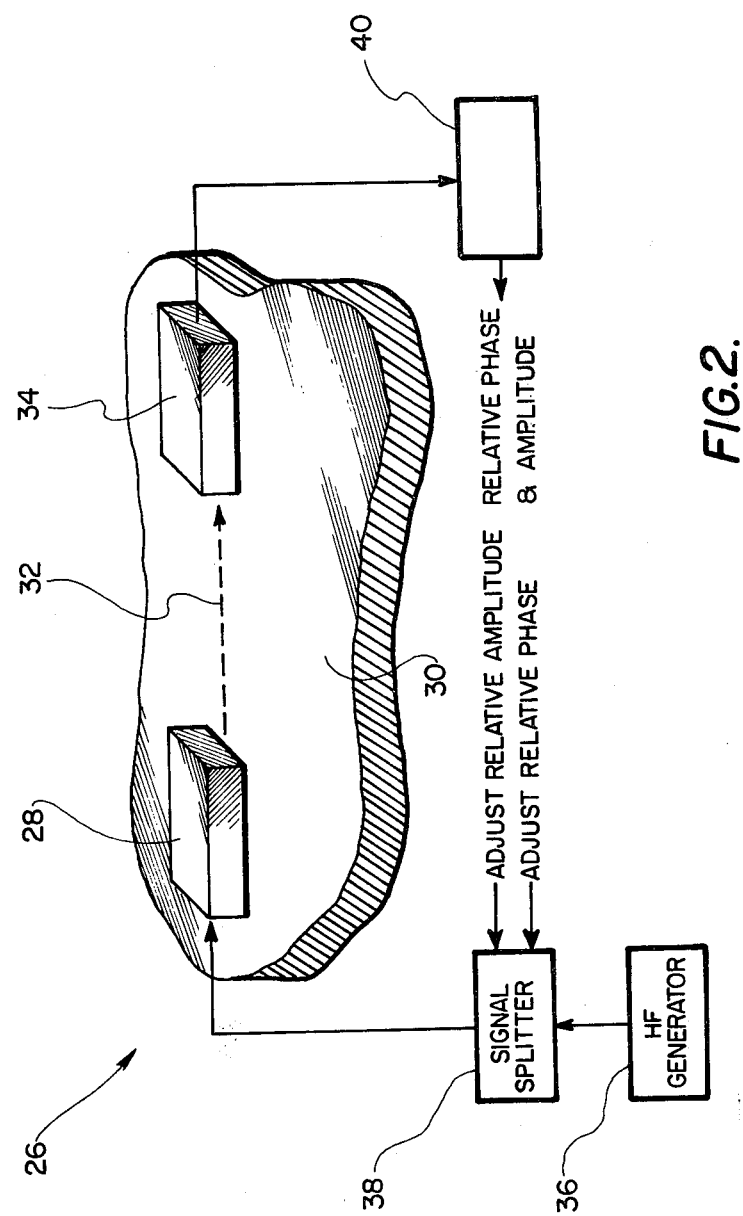
FIG. 2 is a schematic view illustrating an ultrasonic ellipsometer constructed according to the present invention.

FIG. 2 illustrates how this elliptical polarization principle may be applied to construct an ultrasonic ellipsometer 26. A dual coil transmitting transducer 28 is utilized for generating an elliptically polarized shear wave in an electrically conductive medium, such as the plate 30. The polarized wave, the direction of which is represented by the dashed line 32, propagates in the plate and is detected by a receiving transducer 34. The design of the electromagnetic acoustic transducer 10, illustrated in FIG. 1, may be utilized for both the transmitting transducer 28 and the receiving transducer 34.

The transducer 28 is driven by a high frequency signal generator 36, through a signal splitter 38. The signal splitter divides the driving signal for application to each of the two orthogonal coils of the transducer and provides a means for controlling the polarization of the generated wave by affording adjustment of the relative amplitude and phase of the signals which are applied to the two coils.

The resulting wave is detected by the receiving transducer 34, the output of which is applied to a signal analyzer 40, which compares the individual output signal from each of the coils of the transducer 34 and provides an indication of the polarization of the composite wave. In this manner, the ellipsometer 26 can be utilized to measure properties of the plate 30 which cause a change in the polarization of an ultrasonic wave traveling in the material.

The ellipsometer 26 can be utilized in conjunction with a thick material sample by exciting a tone burst which propagates through the material, reflects from the back surface, and is then detected by the receiver. It is frequently desirable, however, to obtain measurements on a thinner plate for which such a tone burst would be too long to allow resolution of the individual reflections. In the latter case, a guided wave model of the wave propagation is more useful.

Figure 3:
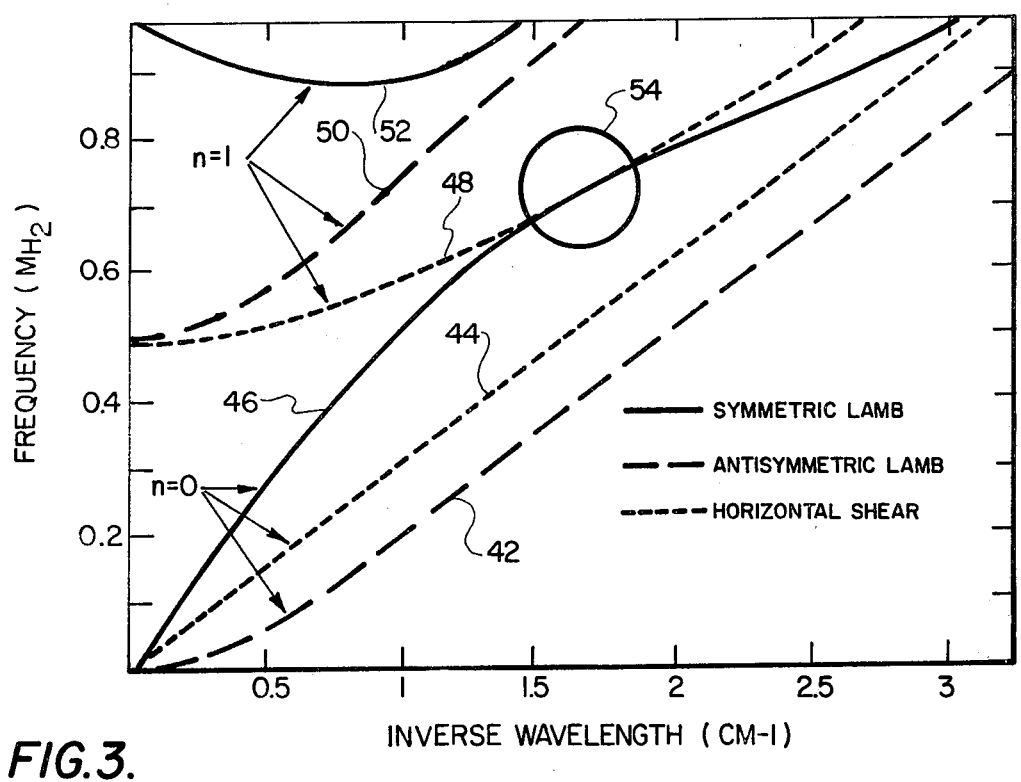
FIG. 3 graphically illustrates the dispersion curves which facilitate the operation of the present invention in a relatively thin, plate type of material.

The guided wave model is portrayed in FIG. 3, which is a graphical illustration of the dispersion curves for some of the guided wave modes which will propagate in a 0.125 inch thick aluminum plate. Curves 42, 44, and 46 represent the fundamental order curves for the antisymmetric Lamb, horizontal shear, and symmetric Lamb waves, respectively. Curves 48, 50, and 52 represent the dispersion curves for the first higher order modes (n=1) of the horizontal shear, antisymmetric Lamb, and symmetric Lamb waves, respectively. As can be seen from FIG. 3, two wave modes do not generally coexist with equal phase and equal group velocity, which are each necessary conditions for obtaining ellipsometric operation. In one region of the frequency spectrum, however, which is approximately within the area 54, there is a point of tangency between the first higher mode (n=1) horizontal shear mode and the fundamental (n=0) symmetric Lamb mode. At this tangent point, each mode may be decomposed into plane shear waves which are reverberating at 45° between the faces of a plate. Therefore, these two modes will propagate with equal phase and group velocities at that point. This phenomenon occurs because, at incidence and reflection angles of 45°, the vertical shear wave will be entirely reflected with no mode conversion to evanescent longitudinal waves. An ellipsometer can be made to operate at this point by selecting transducers with a period which is twice the thickness of the plate to be tested.

Several tests were conducted to evaluate the usefulness of the method of this invention for ultrasonic applications. In these tests, the transducers utilized differed slightly from the transducer 10 illustrated in FIG. 1 in that two separate transmitting transducers were placed side-by-side (one for vertical shear and one for horizontal shear waves) and measurements were obtained with two side-by-side receiving transducers. In the far field, where the beams from the separate transducers overlapped, this design is equivalent to that shown in FIG. 1. A tone burst of 0.69 MHz was impressed on each of the two transmitting transducers with equal phase so that orthogonal waves were radiated at $\theta = 45°$ in a 0.125 inch aluminum plate. The outputs of the receiving transducers were combined after suitable amplification. For these experiments, a null output format was chosen, in which the phase and amplitude of the input signals were fixed, while the phase and amplitude of the received signals were adjusted to produce a null output. Changes in physical properties were thus indicated by a deviation from the null.

The theory of operation of such a device may be deduced from a form of the wave equation. In the null mode, the output S is $$[A_1 e^{-j(k_1+\alpha_1)x} - A_2 e^{-j(k_2+\alpha_2)x}] e^{j\omega t} \quad (2)$$

where $\omega$ is the angular frequency, $k_1$ and $k_2$ are the propagation constants of the two modes, $\alpha_1$ and $\alpha_2$ are the attenuations of the two modes, and $A_1$ and $A_2$ are complex amplitude factors which can be adjusted to null the device (S=0) under particular conditions.

Operation on an isotropic plate at the frequency indicated in FIG. 3 within the area 54 will produce a null output when $A_1 = A_2$, since $\alpha_1 = \alpha_2$ and $k_1 = k_2$ at this tangent frequency. Changes in the properties of the wave-conducting material will then produce a nonzero value of S which will be determined by changes in the propagation constants and/or attenuation. Several effects can produce a degradation of the null. Since guided waves are dispersive, the null condition can be exactly established at only a single frequency. Consequently, continuous wave, or long tone burst, operation is desirable. The length L of the tone burst should be chosen so that $\Delta kL << \pi$, where $\Delta k$ is the mismatch between the wave vectors at the bounds of the spectrum of the driving signal. Larger propagation distances require greater monochromaticity and hence, longer pulse durations.

Figure 4:
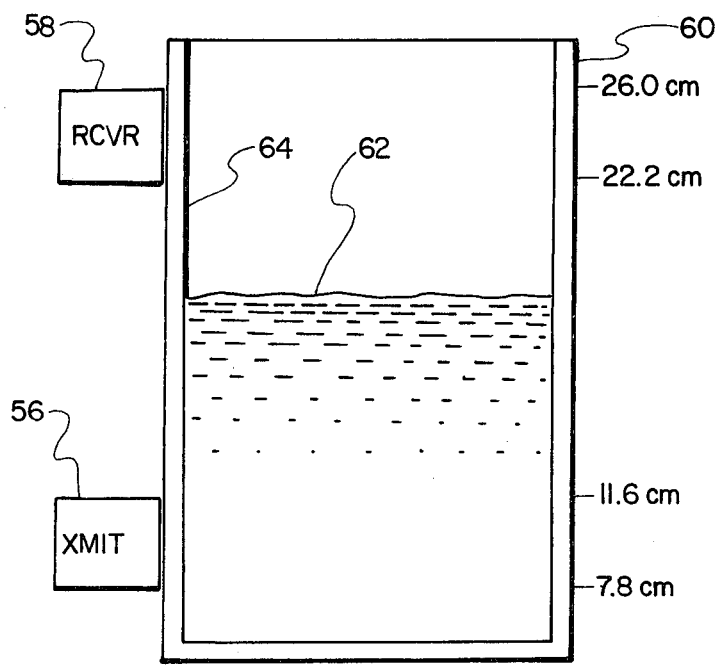
FIG. 4 is a vertical cross-sectional view illustrating the use of the present invention to measure fluid depth.

Many applications for the ultrasonic ellipsometer apparatus described above may be envisioned. In a first application, illustrated in FIG. 4, the ellipsometer, consisting of dual transmitting transducers 56 and dual receiving transducers 58, is mounted on the outside surface of a vessel 60 containing a variable quantity of water 62. In a particular example of this application, the mounting wall 64 was made of a 0.125 inch aluminum plate so that the effect of a fluid on the surface opposite the transducers could be measured. This application demonstrates the sensitivities of the different wave types to mechanical changes at the surface of the plate. A horizontally polarized shear (SH) wave will be unaffected by the presence of water at the plate surface because a fluid does not support shear stresses. The vertically polarized shear (SV) wave, however, will be absorbed since the surface displacement resulting from the normal component of the n=0 Lamb mode will couple to a longitudinal wave radiating into the fluid. Thus, the null output will be changed due to the preferential absorption of one wave caused by a change in the surface condition of the plate.

Figure 5:
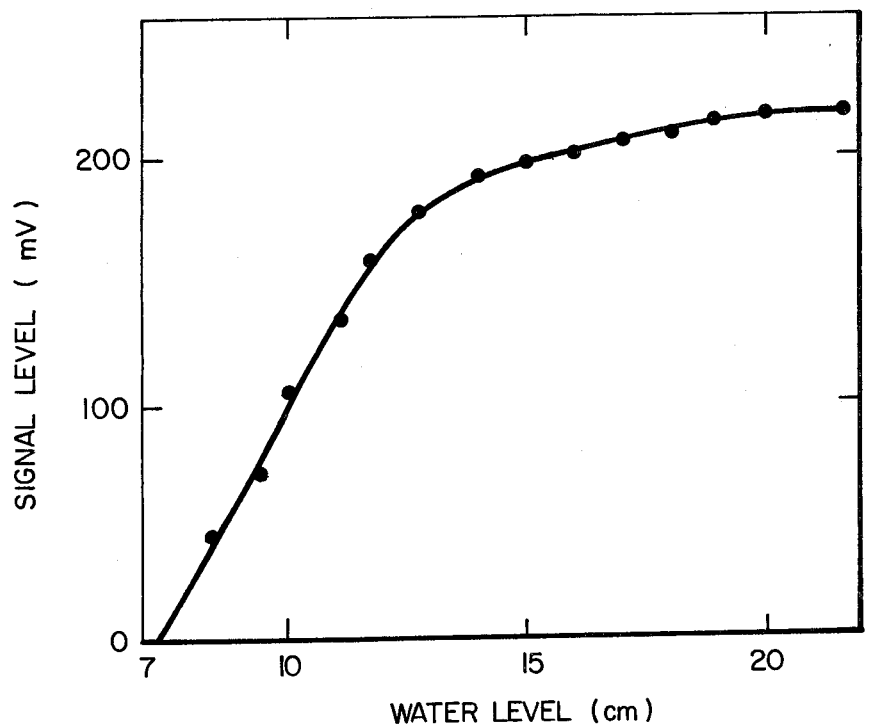
FIG. 5 is a graphical illustration of the results of a fluid depth measurement using the present invention.

FIG. 5 provides a graphical illustration of a null signal which was obtained by establishing a null with no water in the vessel 60, then making measurements for various water levels in the vessel. The indicated signal variation establishes the expected behavior and confirms the utility of the ultrasonic ellipsometer for detecting changes in surface conditions.

Figure 6:
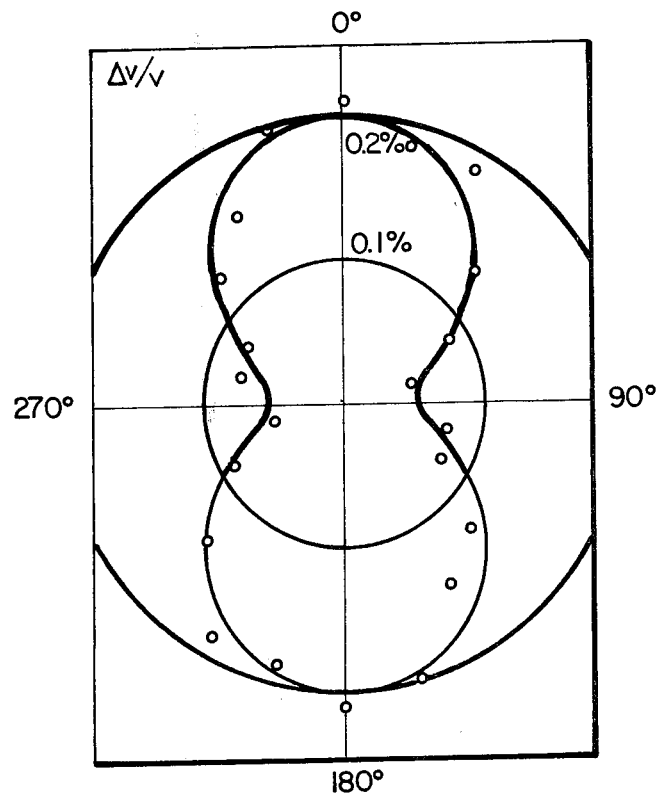
FIG. 6 is a graphical illustration portraying the use of the present invention to detect bulk changes introduced in a material by a rolling process.

In a second application, the inventive technique may be utilized to sense the anisotropic elastic properties of a rolled plate. Such properties can be related to the preferential orientation of the grains, i.e., the texture, produced by the rolling process. The changes in output in this type of material, such as aluminum, will occur as a result of changes in velocity (changes in $k_1$ and $k_2$) rather than changes in attenuation. These changes are produced because of bulk, rather than surface, properties of the medium. FIG. 6 illustrates the directional dependence of velocity, introduced as a result of the rolling process, plotted as the ratio of the change in velocity to the velocity. The velocity shift was derived from measured data utilizing equation (2). Assuming that the values of $\alpha$, $k$, and $A$ are approximately the same for the two modes, the resulting relationship is $$\Delta V/V = S/AkL \quad (3)$$

where L=the propagation distance. This technique may be used to readily measure rather small veocity changes.

Thus a new technique for exciting shear waves of arbitrary polarization has been described, with many potential applications including measuring the fluid level in a closed vessel and monitoring the texture of plates during rolling to ensure the maintenance of acceptable mechanical properties. Many additional applications may be envisioned because of the potential which the invention provides for a high precision measurement of a variety of elastic properties, using a device which requires no mechanical coupling and thus is suitable for use under many adverse operating conditions.

In conclusion, although typical embodiments of the present invention has been illustrated and discussed above, numerous modifications and alternative embodiments of the apparatus and method of this invention will be apparent to those skilled in the art in view of this description. Accordingly, this description is to be considered as illustrative only and is provided for the purpose of teaching those skilled in the art the manner of constructing the apparatus and performing the method of this invention. Furthermore, it should be understood that the forms of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit attained through reading the above description of the invention.

What is claimed is:

1. An electromagnetic acoustic transducer for generating and detecting an elliptically polarized ultrasonic wave in an electrically conductive material, comprising:
   a source of magnetic flux for establishing a magnetic field directed normal to a surface of said material and periodic in intensity in a direction perpendicular to said field direction;
   a first conductor for inducing a first alternating current in a first current direction within said material perpendicular to said field direction and perpendicular to said periodic direction; and
   a second conductor for inducing a second alternating current in a second current direction within said material perpendicular to said field direction and parallel to said periodic direction.

2. The transducer of claim 1, wherein said source of magnetic flux comprises a row of alternately oriented magnets.

3. The transducer of claim 2, wherein:
   said first conductor comprises a first coil coaxially wound around said row; and
   said second conductor comprises a second coil wound around said row orthogonal to said first coil.

4. The transducer of claim 3, wherein said row comprises a plurality of uniformly sized, adjacent permanent magnets.

5. An electromagnetic acoustic transducer for generating and detecting an elliptically polarized ultrasonic wave in an electrically conductive material, comprising:
   a row of uniformly sized, adjacent, alternately oriented permanent magnets;
   a first coil coaxially wound around said row; and
   a second coil wound around said row orthogonal to said first coil.

6. An electromagnetic acoustic transducer for generating an elliptically polarized ultrasonic wave in an electrically conductive material, comprising:
   means for establishing a magnetic field directed normal to a surface of the material and periodic in intensity in a direction perpendicular to said field direction;
   means disposed between said magnetic field means and said surface for inducing a first alternating current in a first current direction within said material perpendicular to said periodic direction; and
   means disposed between said magnetic field means and said surface for inducing a second alternating current in a second current direction within said material perpendicular to said field direction and parallel to said periodic direction.

7. An ultrasonic ellipsometer, comprising:
   a transmitting transducer for generating an elliptically polarized ultrasonic wave in an electrically conductive material, including
   a first source of magnetic flux for establishing a first magnetic field directed normal to a surface of said material and periodic in intensity in a direction perpendicular to said first field direction,
   a first transmitting conductor for inducing an alternating current in a direction within said material perpendicular to said first field direction and perpendicular to said periodic direction, and
   a second transmitting conductor for inducing an alternating current in a direction within said material perpendicular to said first field direction and parallel to said periodic direction; and
   a receiving transducer for detecting said polarized wave in said material, including
   a second source of magnetic flux for establishing a second magnetic field directed normal to said surface and periodic in intensity in a direction perpendicular to said second field direction,
   a first receiving conductor for detecting an alternating current in a direction within said material perpendicular to said second field direction and perpendicular to said periodic direction, and
   a second receiving conductor for detecting an alternating current in a direction within said material perpendicular to said second field direction and parallel to said periodic direction.

8. The ellipsometer of claim 7, further comprising:
   a high frequency signal generator for driving said transmitting transducer; and
   a signal splitter for coupling said generator to said first and second transmitting conductors with a variable relative amplitude and phase, thereby controlling the polarization of said generated wave.

9. The ellipsometer of claim 8, further comprising a signal analyzer connected to said first and second receiving conductors for indicating the polarity of said detected wave.

10. An ultrasonic ellipsometer, comprising:
    a transmitting transducer for generating an elliptically polarized ultrasonic wave in an electrically conductive material, including
    a first source of magnetic flux for establishing a first magnetic field directed normal to a surface of said material and periodic in intensity in a direction perpendicular to said first field direction,
    a first transmitting conductor for inducing an alternating current in a direction within said material perpendicular to said first field direction and perpendicular to said periodic direction, and
    a second transmitting conductor for inducing an alternating current in a direction within said material perpendicular to said first field direction and parallel to said periodic direction;
    a receiving transducer for detecting said polarized wave in said material, including
    a second source of magnetic flux for establishing a second magnetic field directed normal to said surface and periodic in intensity in a direction perpendicular to said second field direction,
    a first receiving conductor for detecting an alternating current in a direction within said material perpendicular to said second field direction and perpendicular to said periodic direction, and
    a second receiving conductor for detecting an alternating current in a direction within said material perpendicular to said second field direction and parallel to said periodic direction;

a high frequency signal generator for driving said transmitting transducer;

a signal splitter coupling said signal generator to said transmitting transducer for controlling the polarization of said generated wave; and a signal analyzer connected to said receiving transducer for indicating the polarity of said detected wave.

11. A method for generating an elliptically polarized ultrasonic shear wave in an electrically conductive material, comprising the steps of:

establishing a magnetic field directed normal to a surface of the material and periodic in intensity in a direction parallel to the surface;

inducing in the material and within the magnetic field a first alternating current in a first current direction perpendicular to the field direction and perpendicular to the periodic direction, the magnetic field and the first current interacting to produce a vertical shear ultrasonic wave in the material; and inducing in the material and within the magnetic field a second alternating current in a second current direction within the material perpendicular to the field direction and parallel to the periodic direction, the magnetic field and the second current interacting to produce a horizontal shear wave in the material.

12. The method of claim 11, further comprising the step of:

controlling the amplitude and phase of the first alternating current relative to the second alternating current to adjust the polarization of the generated wave.

13. The method of claim 12, wherein the material is relatively thick in the direction of the magnetic field.

14. The method of claim 12, wherein the material is a bounded plate which is relatively thin in the direction of the magnetic field.

* * * * *